United States Patent
Ahari

(10) Patent No.: US 6,685,735 B1
(45) Date of Patent: Feb. 3, 2004

(54) SYENT/GRAFT DEPLOYMENT CATHETER WITH A STENT/GRAFT ATTACHMENT MECHANISM

(75) Inventor: Frederick Ahari, Clearwater, FL (US)

(73) Assignee: Endovascular Technologies, Inc., Santa Clara, CA (US)

( * ) Notice: Subject to any disclaimer, the term of this patent is extended or adjusted under 35 U.S.C. 154(b) by 25 days.

(21) Appl. No.: 09/602,161

(22) Filed: Jun. 22, 2000

Related U.S. Application Data

(63) Continuation of application No. 09/050,146, filed on Mar. 30, 1998, now Pat. No. 6,102,942.

(51) Int. Cl.⁷ .................................................. A61F 2/06
(52) U.S. Cl. ...................... 623/1.11; 623/1.13; 623/1.23
(58) Field of Search ............................... 623/1.11, 1.23, 623/1.36, 1.39, 1.4, 1.44, 1.45, 1.46, 1.12, 1.13, 1.15; 606/194, 195, 198, 200

(56) References Cited

U.S. PATENT DOCUMENTS

| | | | |
|---|---|---|---|
| 4,307,723 A | * 12/1981 | Finney | 128/349 R |
| 4,562,596 A | 1/1986 | Kornberg | |
| 4,681,110 A | 7/1987 | Wiktor | |
| 5,078,720 A | 1/1992 | Burton et al. | |
| 5,360,414 A | * 11/1994 | Yarger | 604/264 |
| 5,403,341 A | 4/1995 | Solar | |
| 5,496,277 A | 3/1996 | Termin et al. | |
| 5,591,197 A | * 1/1997 | Orth | 623/1.11 |
| 5,720,726 A | * 2/1998 | Marcadis et al. | 604/96 |
| 5,735,859 A | 4/1998 | Fischell et al. | |
| 5,738,654 A | * 4/1998 | Tihon | 604/105 |
| 5,746,745 A | * 5/1998 | Abele et al. | 606/108 |
| 5,797,952 A | * 8/1998 | Klein | 606/198 |
| 5,824,036 A | 10/1998 | Lauterjung | |
| 5,893,867 A | * 4/1999 | Bagaoisan et al. | 606/198 |
| 5,913,871 A | * 6/1999 | Werneth et al. | 606/194 |
| 5,954,729 A | * 9/1999 | Bachmann et al. | 606/108 |
| 6,071,305 A | * 6/2000 | Brown et al. | 623/1 |
| 6,132,458 A | * 10/2000 | Staehle | 623/1.11 |
| 6,149,680 A | * 11/2000 | Shelso | 623/1.11 |
| 6,187,013 B1 | * 2/2001 | Stoltze et al. | 606/108 |
| 6,190,404 B1 | * 2/2001 | Palmaz et al. | 623/1.15 |
| 6,203,547 B1 | * 3/2001 | Nguyen | 623/1.11 |
| 6,214,036 B1 | * 4/2001 | Letendre et al. | 623/1.11 |
| 6,228,110 B1 | * 5/2001 | Munsinger | 623/1.11 |
| 6,231,597 B1 | * 5/2001 | Deem | 623/1.11 |
| 6,241,758 B1 | * 6/2001 | Cox | 623/1.11 |
| 6,309,411 B1 | * 10/2001 | Lashinski et al. | 623/1.1 |

FOREIGN PATENT DOCUMENTS

| | | |
|---|---|---|
| DE | 2980304 | 4/1998 |
| WO | WO 93/1182 | 6/1993 |
| WO | WO 98/0958 | 3/1998 |

* cited by examiner

*Primary Examiner*—Bruce Snow
*Assistant Examiner*—Cheryl Miller
(74) *Attorney, Agent, or Firm*—Fulwider Patton Lee Utecht, LLP

(57) ABSTRACT

A stent/graft deployment catheter which deploys a stent/graft by pulling it out of its delivery sheath rather than pushing it out. The stent/graft deployment catheter comprises a tip capable of positively engaging a distal end of a stent/graft. Said tip houses a pair of ball bearings which engage a notch in the inner surface of the stent/graft when the inner lumen is occupied by a guide wire.

6 Claims, 10 Drawing Sheets

SYENT/GRAFT DEPLOYMENT CATHETER WITH A STENT/GRAFT ATTACHMENT MECHANISM

This application is a continuation of U.S. application Ser. No. 09/050,146, filed Mar. 30, 1998, now U.S. Pat. No. 6,102,942.

BACKGROUND OF THE INVENTION

1. Field of the Invention

The invention relates to a stent/graft deployment catheter, particularly for repairing defects in arteries and other lumens within the body. More particularly, the invention relates to a stent/graft deployment catheter, having a positive stent attachment mechanism on its distal end, for delivering a stent/graft in situ for repairing defective body lumens, and particularly abdominal aortic aneurysms.

2. Description of the Prior Art

An abdominal aortic aneurysm (AAA) is a sac caused by an abnormal dilatation of the wall of the aorta as it passes through the abdomen. The aorta is the main artery of the body, supplying blood to all organs and parts of the body except the lungs. It arises from the left ventricle of the heart, passes upward, bends over and passes down through the thorax and through the abdomen, and finally divides into the iliac arteries which supply blood to the pelvis and lower extremities.

The AAA ordinarily occurs in the portion of the aorta below the kidneys. When left untreated, the aneurysm will eventually cause the sac to rupture with ensuing fatal hemorrhaging in a very short time. The repair of abdominal aortic aneurysms has typically required major abdominal surgery in which the diseased and aneurysmal segment of the aorta is bridged with a prosthetic device, such as a synthetic graft.

As with all major surgeries, there are many disadvantages to the above mentioned surgical technique, the foremost of which is the high mortality and morbidity rate associated with surgical intervention of this magnitude. Other disadvantages of conventional surgical repair include the extensive recovery period associated with such surgery; difficulties in suturing the graft to the aorta; the unsuitability of the surgery for many patients, particularly older patients exhibiting comorbid conditions; and the problems associated with performing the surgical procedure on an emergency basis after the aneurysm has already ruptured.

In view of the above mentioned disadvantages of conventional surgical repair techniques, techniques have been developed for repairing AAAs by intraluminally delivering an aortic graft to the aneurysm site through the use of a catheter based delivery system, and securing the graft within the aorta using an expandable stent. Since the first documented clinical application of this technique was reported by Parodi et al. in the Annals of Vascular Surgery, Volume 5, pages 491–499 (1991), the technique has gained more widespread recognition and is being used more commonly. As vascular surgeons have become more experienced with this endovascular technique, however, certain problems have been encountered. One major problem involves deployment of the stent/graft. Substantial friction between the outer surface of the graft material and the inner surface of the delivery sheath of the deployment catheter makes it sometimes difficult to deploy the stent/graft device precisely in the right location while not exerting significant forces which may damage the stent/graft device. The traditional expandable stent/graft is radially compressed before insertion into the delivery sheath. The more the stent/graft device can be compressed the smaller the introducer sheath and the catheter can be made. Therefore, a highly compressible stent/graft is desired. One problem with radially compressing a given stent/graft to its maximum extent is that once the compressed stent/graft is inserted into the delivery sheath of the catheter, friction between the outer surface of the graft and the inner surface of the delivery sheath, caused by the restoring force of the compressed stent/graft, makes it very difficult to push the stent/graft out of the delivery sheath of the catheter, and therefore, makes it difficult to accurately deploy the stent/graft without damaging it. In light of this design limitation, the total cross sectional area of a traditional expandable stent/graft in its compressed deployment state is generally designed 10% to 30% less than the area of the corresponding delivery sheath in order to limit friction between the graft and the delivery sheath and to ensure that the stent/graft is not damaged upon deployment.

SUMMARY OF THE INVENTION

Accordingly, the need exists for an improved stent/graft capable of being accurately deployed from a delivery sheath having a high friction delivery surface. More particularly, there exists a need for a stent/graft deployment catheter which pulls rather than pushes the stent/graft out of the delivery sheath, and thereby, avoids the application of damaging compressive forces to the stent/graft.

The invention is a stent/graft deployment catheter having a tip capable of positively engaging a distal end of a stent/graft. The tip houses a pair of ball bearings which engage a notch in the inner surface of the stent/graft when the inner lumen is occupied by a guide wire.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
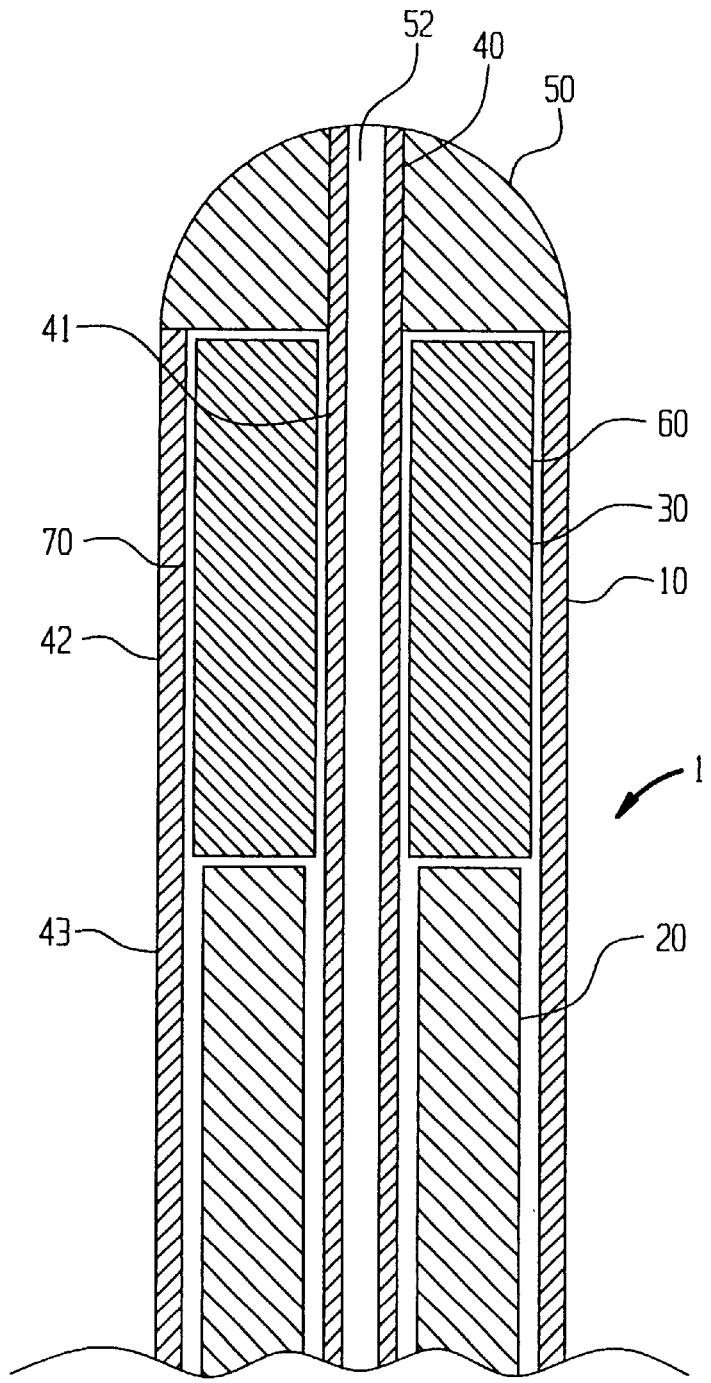
FIG. 1 is longitudinal cross section of a distal portion of a prior art stent/graft deployment catheter.

FIG. 1 illustrates a longitudinal cross section of a co-axial prior art stent/graft deployment catheter, generally designated 1. Said catheter 1 is comprised of a catheter body 10, a tip 50, an inner tube 40, a stent/graft 30, and a plunger 20, all of which are co-axial and have proximal and distal ends. Only the distal portion of the deployment catheter 1 is shown for clarity. The catheter body 10 is slidingly disposed about the inner tube 40 and has a delivery sheath portion 42, a tube portion 43, and an inner surface 70. The plunger 20 is slidingly disposed about the inner tube 40 and is slidingly disposed within the catheter body 10. The distal end of the inner tube 40 is attached to the tip 50. The stent/graft 30 is slidingly disposed about the inner tube 40 and within the delivery sheath portion 42 of the catheter body 10 and is between the proximal end of the tip 50 and the distal end of the plunger 20. The stent/graft 30 has an outer surface 60 and a lumen 52 extending from its proximal end to its distal end. The stent/graft lumen 52 is occupied by a distal portion 41 of the inner tube 40. The delivery sheath portion 42 of the catheter body 10 is located between the tip 50 and the tube portion 43 of the catheter body 10. The inner and outer diameters of the delivery sheath portion 42 and the tube portion 43 are the same.

Figure 2:
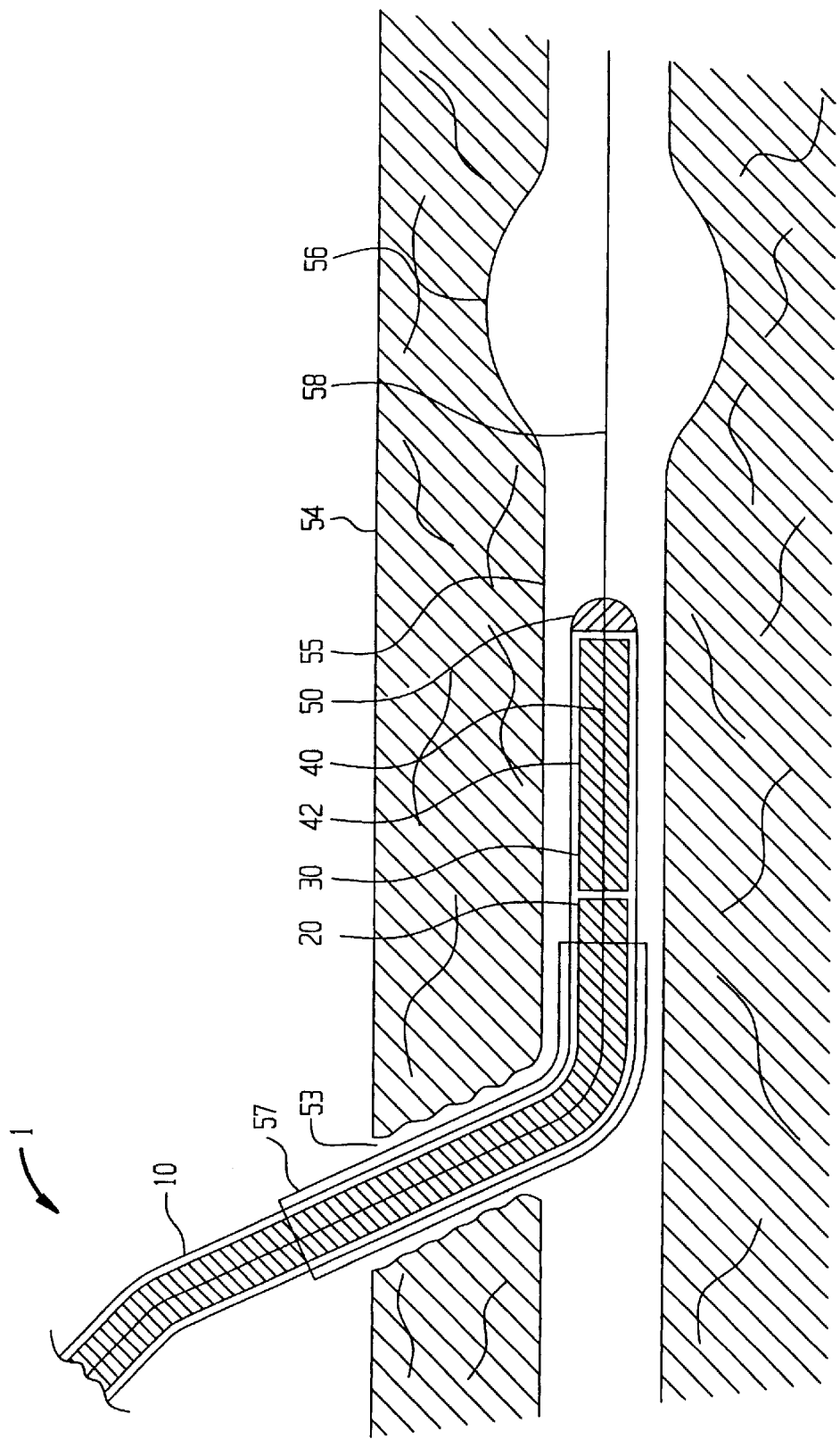
FIG. 2 is a longitudinal cross section of the prior art catheter of FIG. 1 percutaneously inserted into a patient's blood vessel.

The stent/graft deployment catheter 1 may be inserted percutaneously or via a surgical cut-down method into a blood vessel. FIG. 2 illustrates a longitudinal cross section of the prior art catheter 1 percutaneously inserted in a blood vessel 55 of a patient 54. Note that the distal direction is defined relative to the position of the heart; therefore, a distal portion of the catheter 1 is closer to the heart upon insertion than a more proximal portion of the catheter 1. The delivery sheath portion 42 of the catheter 1 is still down stream of an aneurysm 56 in need of repair and has fully exited an introducer sheath 57. If inserted percutaneously, as illustrated in FIG. 2, a guide wire 58 is first advanced through an insertion site 53 into the blood vessel 55 of the patient 54. Next, a dilator sheath assembly (dilator not shown) is disposed about the guide wire 58 and the distal portion of the dilator is used to dilate the insertion site 53. After dilation of the insertion site 53 the dilator is removed while the insertion sheath 57 is held in place in the blood vessel 55 of the patient 54. Next, the catheter 1 is inserted into the introducer sheath 57 and is advanced forward into the blood vessel 55 of the patient 54. Upon proper positioning of the tip 50 in the blood vessel 55 the plunger 20 is held in place while the catheter body 10 is pulled away from the tip 50 exposing the entire stent/graft 30 to blood. Upon contact with blood the stent/graft 30 expands such that the diameter of the stent/graft lumen 52 becomes larger than the outer diameter of the tip 50. The expanded stent/graft 30 becomes fixed in place in the blood vessel 55 and thus bridges the aneurysm. The inner tube 40 is then pulled away from the stent/graft 30 such that the tip 50 passes through the stent/graft lumen 52. Finally, the catheter 1 is removed from the patient 54. Note that there are many other types of self-expandable stent/grafts on the market including heat sensitive and spring-like stent/grafts. Note further that one major function of the introducer sheath 57 is to control bleeding at the insertion site 53 of the patient 54 during the entire procedure.

Figure 3:
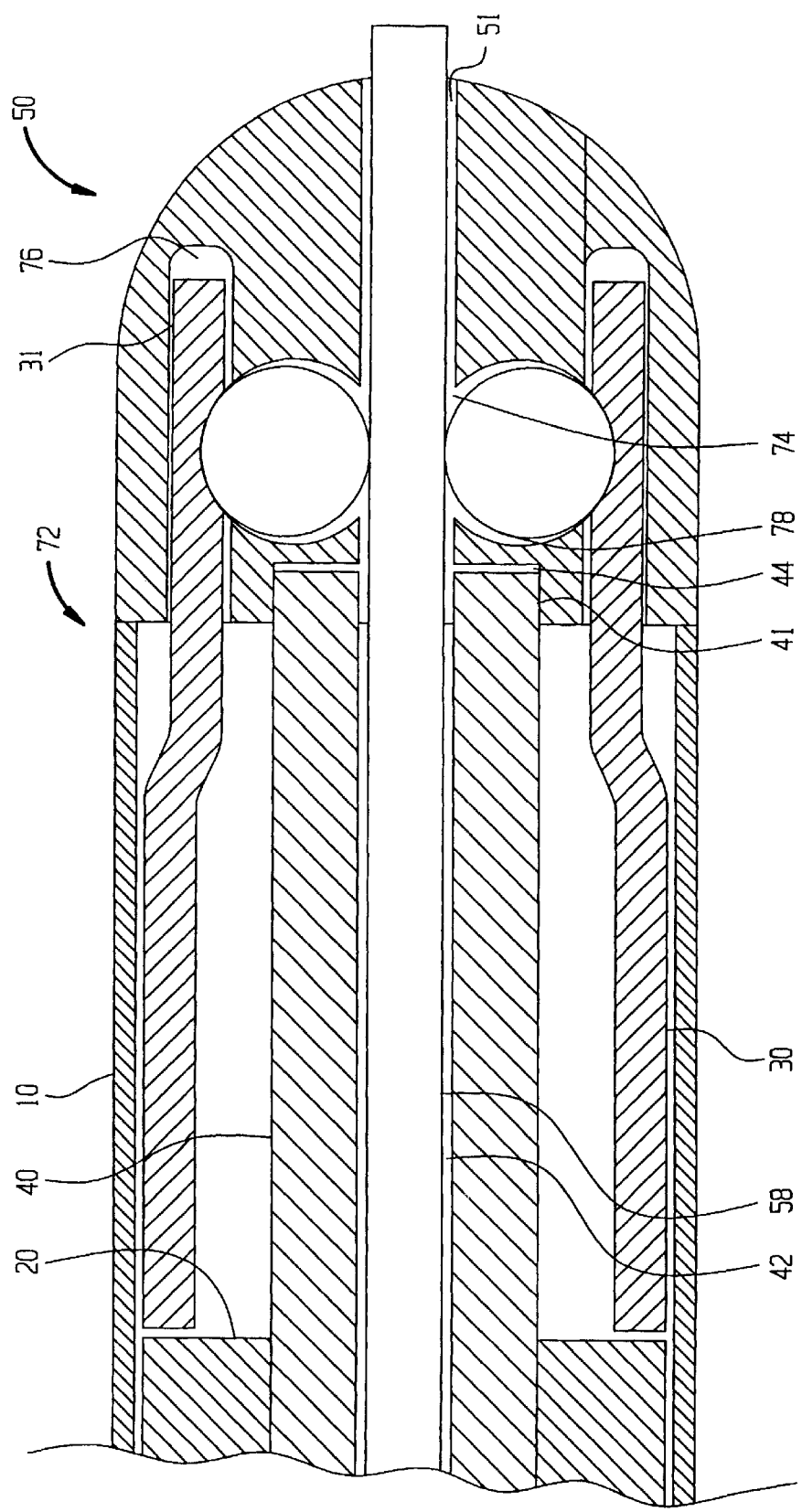
FIG. 3 is a longitudinal cross section of an improved stent/graft deployment catheter having a tip capable of engaging a distal end of a stent/graft.

FIG. 3 illustrates a longitudinal cross section of an improved stent/graft deployment catheter, generally designated 72, comprising a catheter body 10, a plunger 20, an inner tube 40 having a distal portion 41 and a tube inner lumen 42, and a tip 50. Said tip having a tip inner lumen 51, a stent/graft track 76 for accommodating a distal end 31 of a stent/graft 30, a pair of ball bearing chambers 74, a pair of ball bearing 78 contained within said ball bearing chambers 74, and an inner tube cavity 44. The tube inner lumen 42 and the tip inner lumen 51 communicate. The distal portion 41 of the inner tube 40 is disposed within the inner tube cavity 44. A guide wire 58 is disposed within the tube inner lumen 42 and the tip inner lumen 51. The stent/graft 30, as herein defined, may included a stent with a graft attached to it, a stent alone, or a graft alone.

Figure 4:
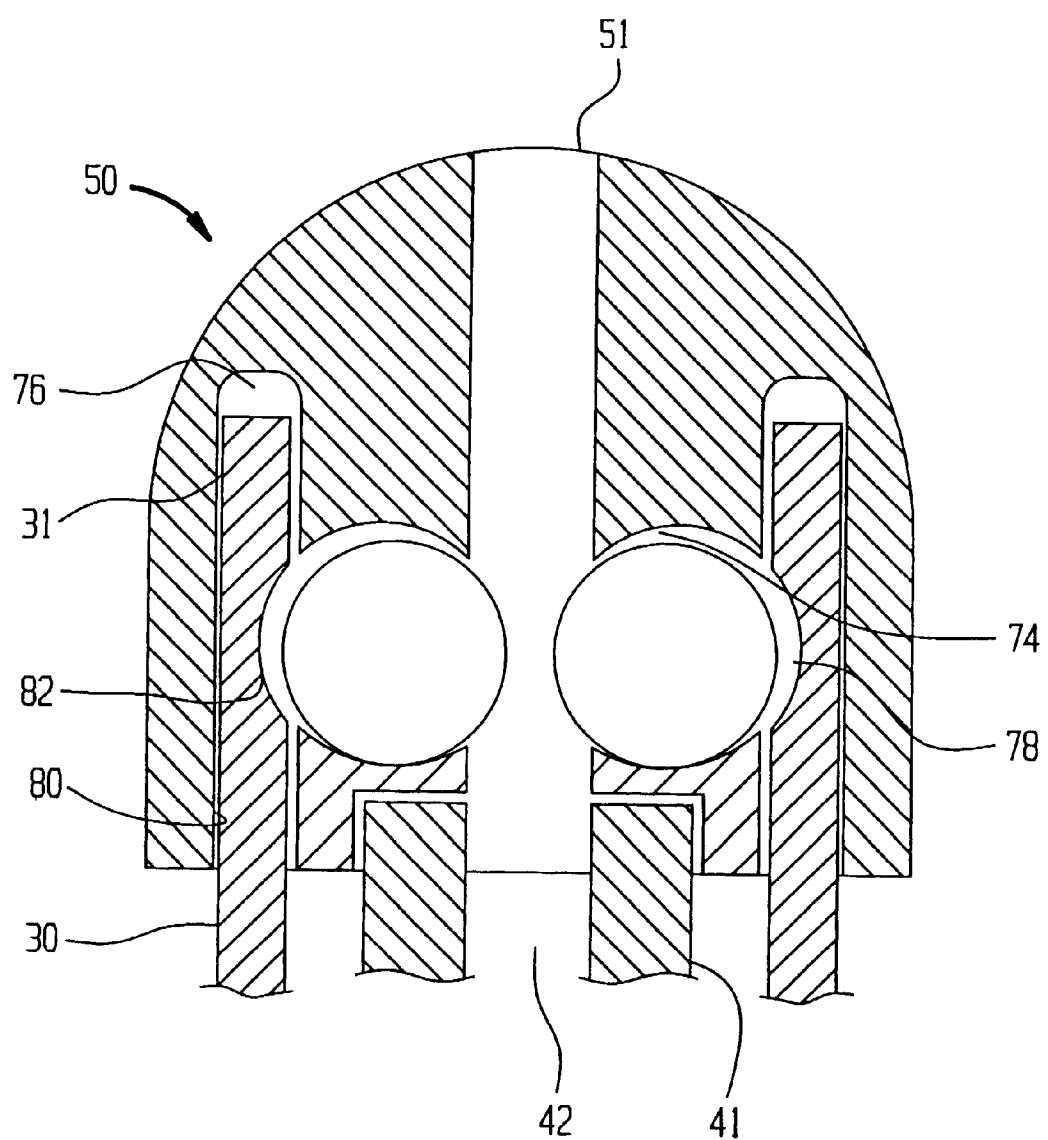
FIG. 4 is a longitudinal cross section of the tip illustrated in FIG. 3 with the ball bearings in a rest position.

FIG. 4 illustrates a longitudinal cross section of the tip 50 without the guide wire 58. Only the distal end 31 of the stent/graft 30 and the distal portion 41 of the inner tube 40 is shown. The stent/graft 30 has an inner surface 80 and a semi-hemispherical notch 82 on said inner surface 80. The ball bearings 78 rest in the ball bearing chambers 74 such that they extend partially into the tip inner lumen 51 and not at all into the stent/graft track 76. In an alternative embodiment of the invention the stent/graft 30 may have a ring connected on one end or a hole in the material making up the stent or graft, comprising the stent/graft 30, for engaging the tip 50. In an alternate embodiment of both the stent/graft 30 and the catheter 72, the tip 50 may engage a groove in the outer surface of the stent/graft 30.

Figure 5:
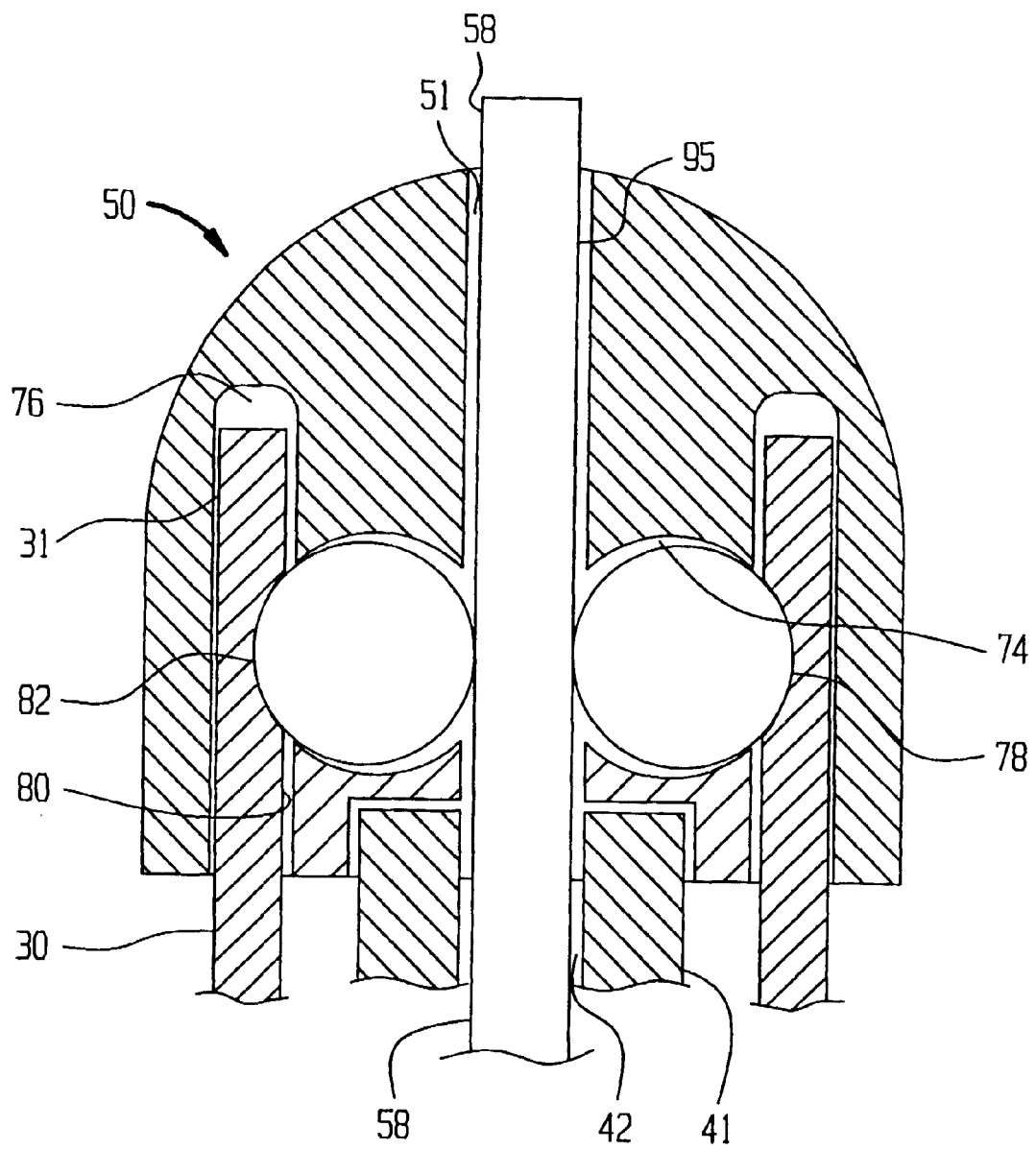
FIG. 5 is a longitudinal cross section of the tip illustrated in FIG. 3 with a guide wire disposed within the inner lumen forcing the ball bearings in a lateral locked position.
Figure 6:
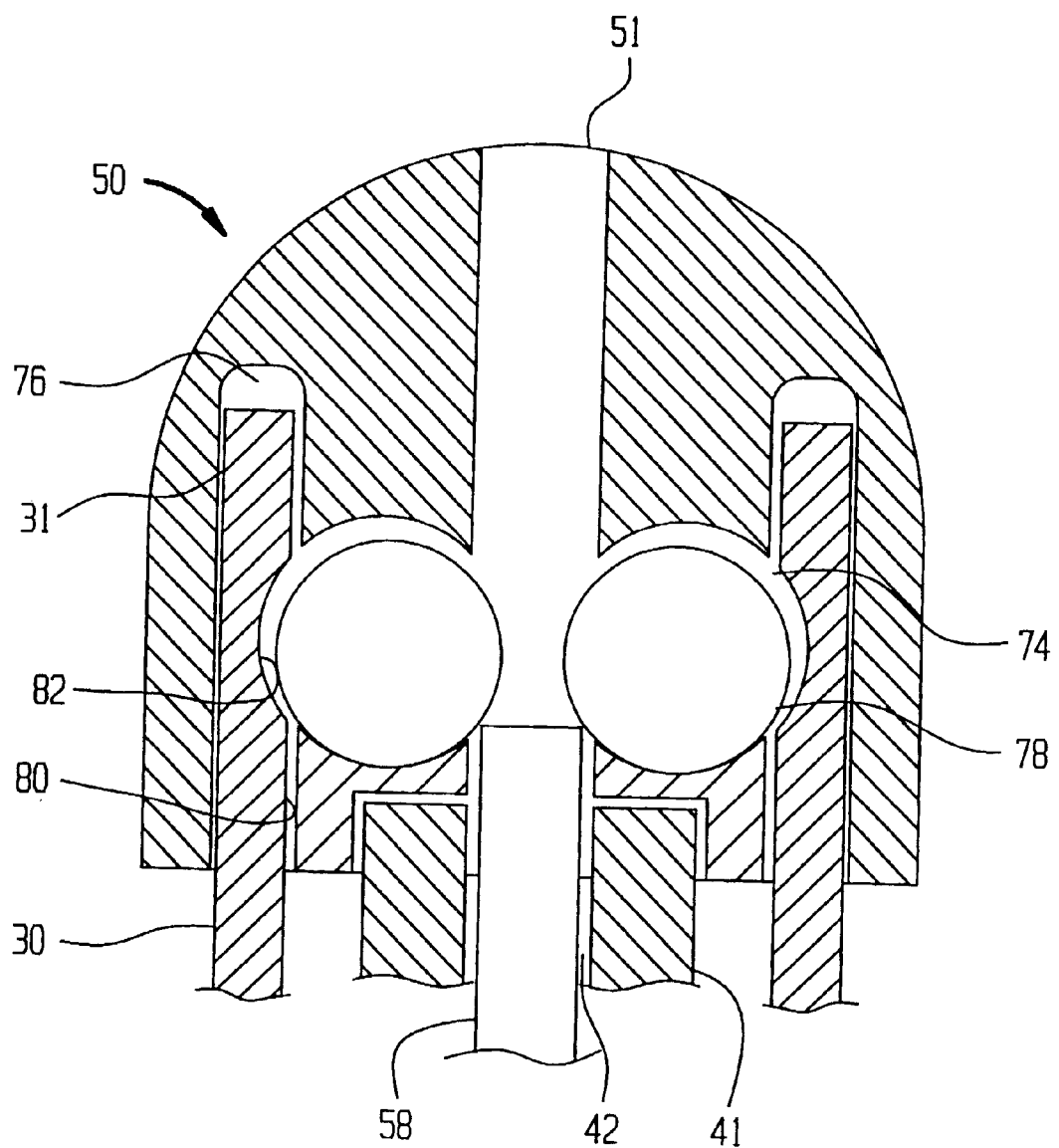
FIG. 6 is a longitudinal cross section of the tip and guide wire illustrated in FIG. 5 with the guide wire moved to a position proximal of the ball bearings.

FIG. 5 illustrates a longitudinal cross section of the tip 50 a with a distal portion 95 of the guide wire 58 disposed within the tip inner lumen 51 and the tube inner lumen 42 and extending beyond a distal end of the tip 50. Again, only the distal end 31 of the stent/graft 30 and the distal portion 41 of the inner tube 40 is shown. The guide wire 58 forces the ball bearings 78 out of their rest position, illustrated in FIG. 4, and into a lateral locked position. The ball bearings 78 in the lateral locked position extend into the stent/graft track 76 and the notch 82. The position of the ball bearings 78 prevents any longitudinal movement of the stent/graft 30 relative to the tip 50, and thereby "locks" the stent/graft 30. "Unlocking" of the stent/graft 30 can be accomplished by removing the guide wire 58 or moving it to a position proximal of the ball bearings 78, as illustrated in FIG. 6, and thus allowing the ball bearings 78 to fall back into their rest unlocked position. Note that the use of one or more ball bearings 78 and one or more ball bearing chambers 74 is anticipated.

Figure 7:
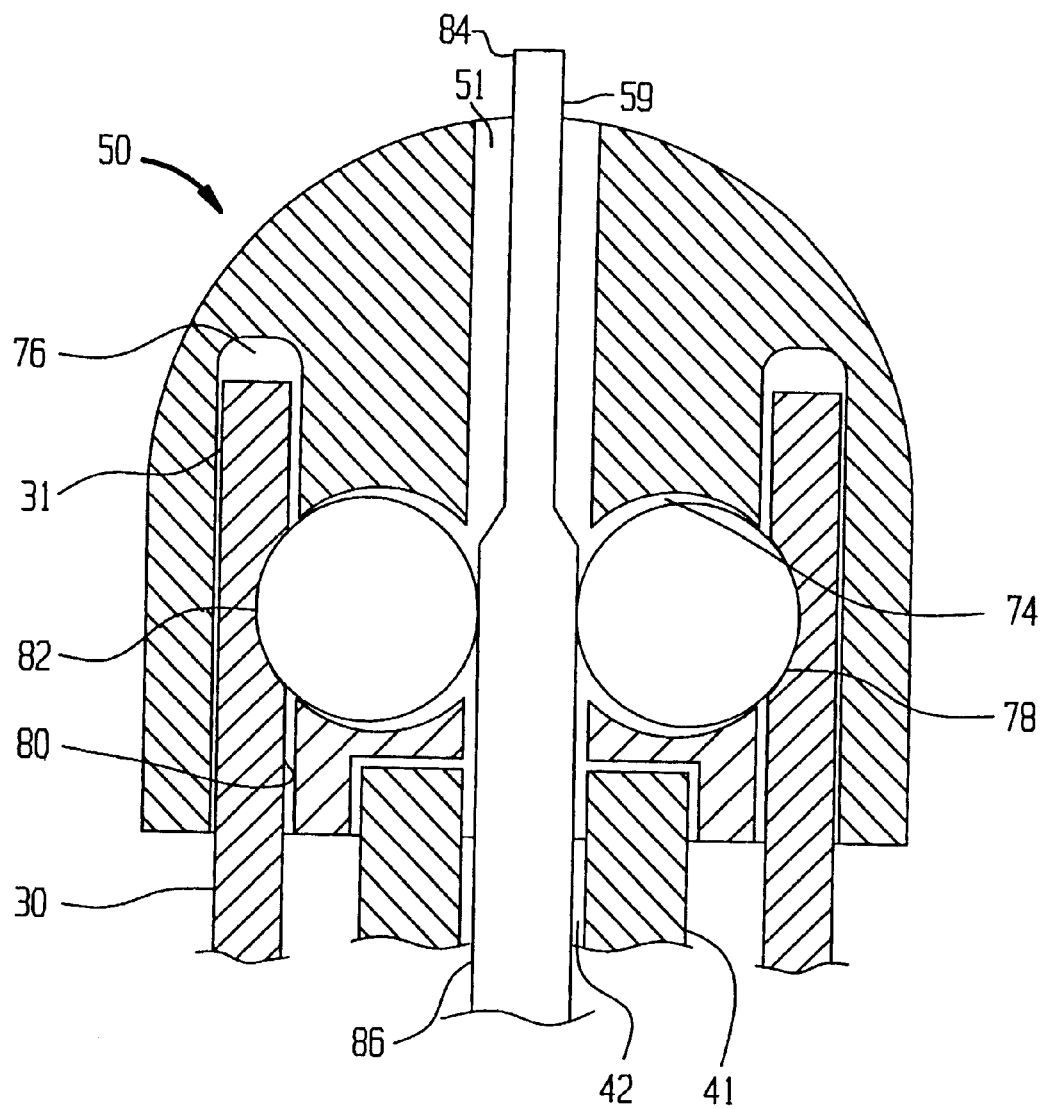
FIG. 7 is a longitudinal cross section of the tip illustrated in FIG. 3 with guide wire of varying diameter disposed within the inner lumen forcing the ball bearings into a lateral locked position.
Figure 8:
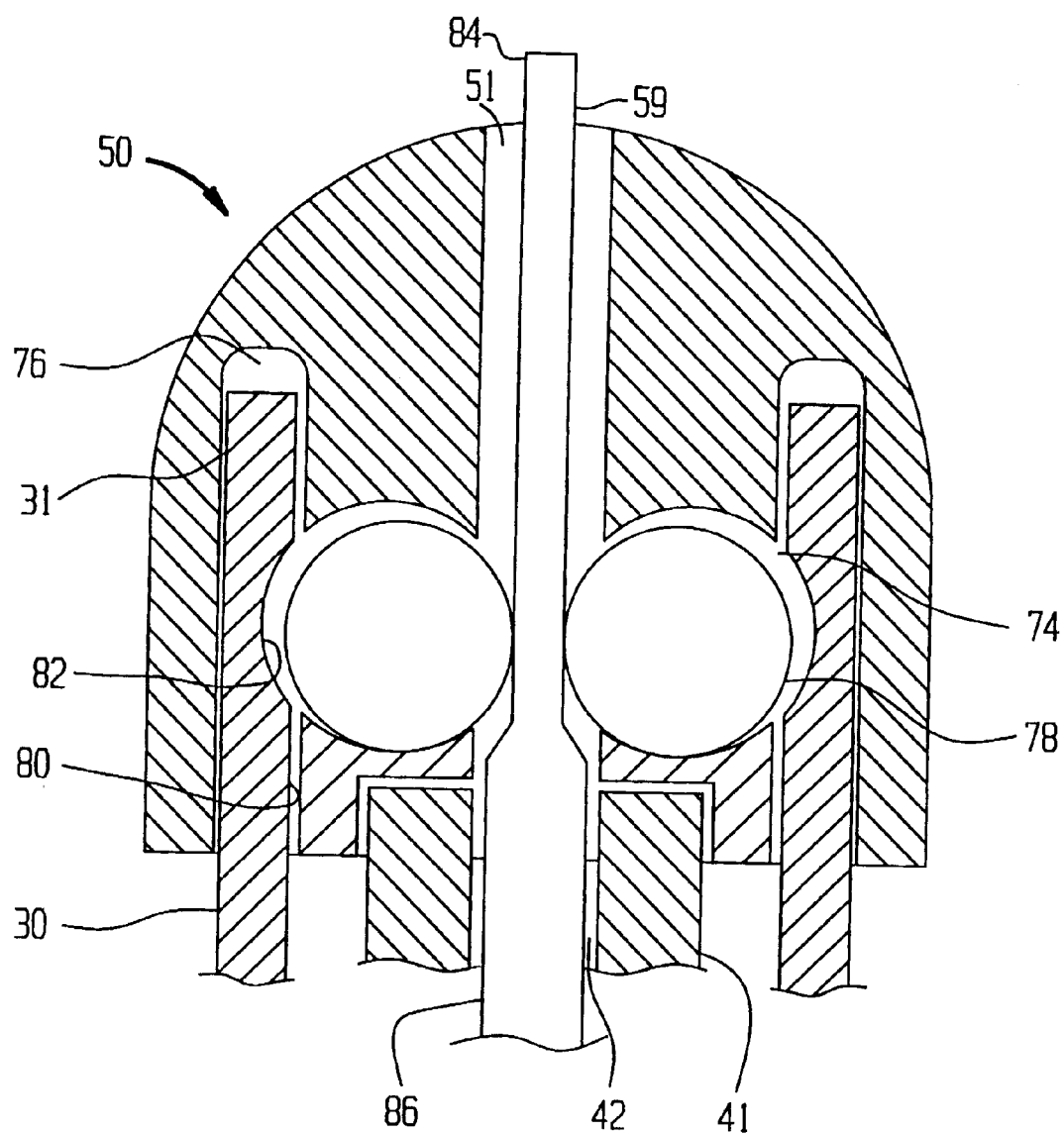
FIG. 8 is a longitudinal cross section of the tip and guide wire illustrated in FIG. 7 with the larger diameter portion of the guide wire moved proximal to the ball bearings.

FIG. 7 illustrates a longitudinal cross section of the tip 50 with a distal portion of an alternative guide wire 59 disposed within the tip inner lumen 51 and the tube inner lumen 42 and extending beyond a distal end of the tip 50. The alternative guide wire 59 has a small diameter portion 84 and a large diameter portion 86. The small diameter portion 84, as illustrated, is disposed within the tip inner lumen 51. The large diameter portion 86, as illustrated, is disposed within the tip inner lumen 51 and the tube inner lumen 42. The large diameter portion 86 of the alternative guide wire 59 forces the ball bearings 78 out of their rest position, illustrated in FIG. 4, and into a lateral locked position. The ball bearings 78 in the lateral locked position extend into the stent/graft track 76 and the notch 82. The position of the ball bearings 78 prevents any longitudinal movement of the stent/graft 30 relative to the tip 50, and thereby "locks" the stent/graft 30. "Unlocking," of the stent/graft 30 can be accomplished by moving the large diameter portion 86 to a position proximal of the ball bearings 78, as illustrated in FIG. 8, and thus allowing the ball bearings 78 to fall back into their rest unlocked position.

Figure 9:
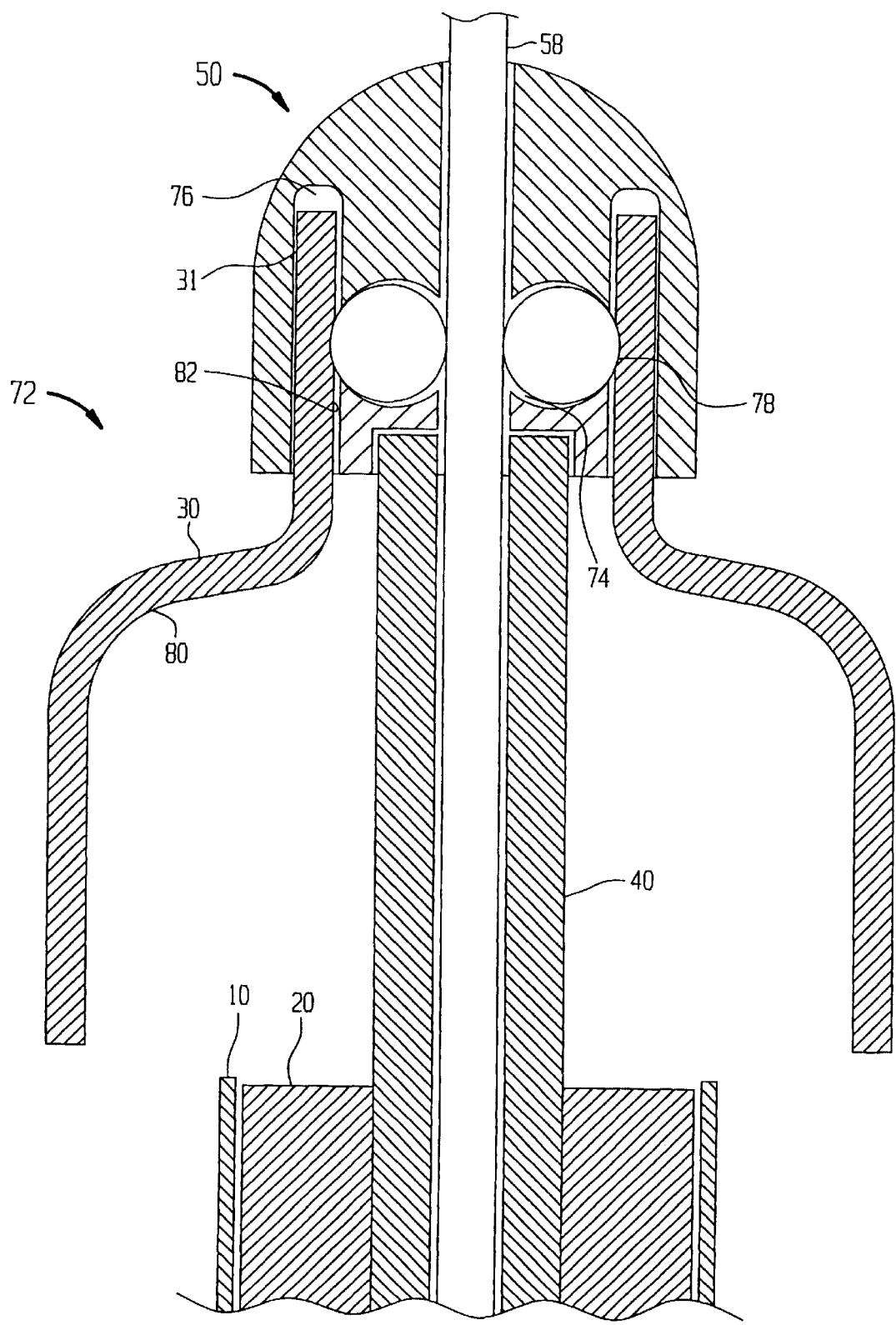
FIG. 9 is a longitudinal cross section of the improved stent/graft deployment catheter, as illustrated in FIG. 3, with the catheter body pulled back, allowing a substantial portion of the stent/graft to radially expand.

FIG. 9 illustrates a longitudinal cross section of the stent/graft deployment catheter 72 with the catheter body 10 pulled back away from the tip 50 allowing the stent/graft 30 to expand. Pulling back the catheter body 10 represents the first stent/graft 30 deployment step after positioning of the stent/graft deployment catheter 72 in the blood vessel 55 (FIG. 2) relative to the aneurysm 56 (FIG. 2). Note that friction between the stent/graft 30 and the catheter body 10 results in nondamaging tensile forces in the body of the stent/graft rather than damaging compressive forces, as produced by the prior art deployment method. The distal end 31 of the stent/graft 30 remains locked in the stent/graft track 76 because of the presence of the guide wire 58. At this point in the deployment procedure the surgeon can fine tune the positioning of the stent/graft 30 relative to the aneurysm 56 (FIG. 2) if necessary. This is in contrast to the prior art catheter, illustrated in FIG. 2, which could not be repositioned after deployment. The stent/graft 30 is not damaged upon deployment because it is pulled out of the catheter body 10 rather than pushed out. After fine tuning the position of the stent/graft in the blood vessel 55 (FIG. 2) relative to the aneurysm 56 (FIG. 2) the surgeon unlocks the distal end 31 of the stent graft 30 by pulling the guide wire 58 to a position proximal of the ball bearing chambers 74, as illustrated in FIG. 6. Upon repositioning of the guide wire 58 the now unlocked distal end 31 of the stent/graft 30 deploys and the stent/graft deployment catheter 72 is removed from the patient 54 (FIG. 2). If the alternative guide wire 59 is used, "unlocking" of the stent/graft 30 is accomplished by moving the large diameter portion 86 to a position proximal of the ball bearings 78.

Figure 10:
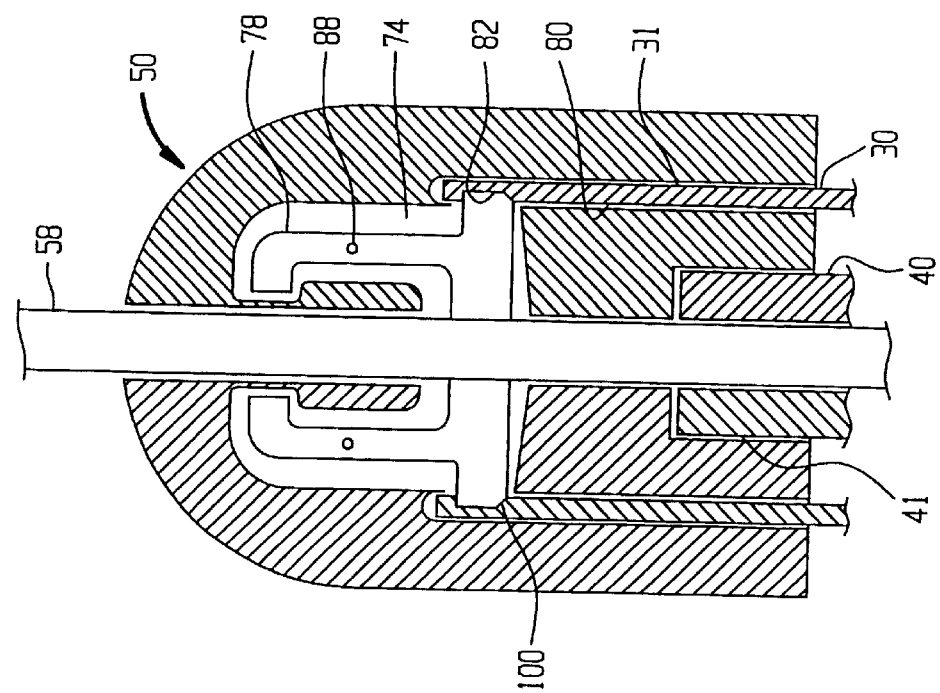
FIG. 10 is a longitudinal cross section of an alternate embodiment of the tip, as illustrated in FIGS. 4–8, with a latch in an unlocked position.
Figure 11:
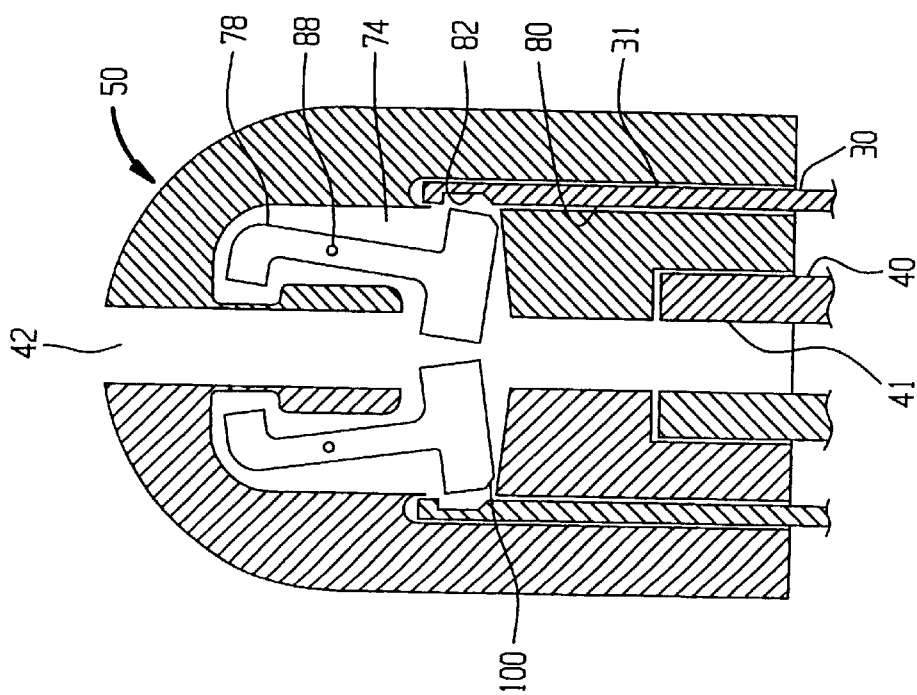
FIG. 11 is a longitudinal cross section of the alternate embodiment of the tip, as illustrated in FIG. 10, with a latch in a locked position.

FIG. 10 illustrates a longitudinal cross section of an alternate tip 50 with an alternate means for locking the stent/graft 30 in the stent/graft track 76. The alternate tip 50 is identical to the tip 50, illustrated in FIG. 4, except that a latch chamber 74 containing a pair of latches 74 replaces the ball bearing chamber 74 (FIG. 4) and the ball bearings 78 (FIG. 4). The latches are pivotally connected to a pivot pin 88 and pivot between an unlocked position, as illustrated in FIG. 10, and a locked position, as illustrated in FIG. 11. Upon insertion of the guide wire 58, as illustrated in FIG. 11, the latches 78 are forced into a locked position preventing any longitudinal movement of the stent/graft 30. In the "locked" position a foot portion 100 of each latch 78 is forced into the notch 82 in the inner surface 80 of the stent/graft 30.

What is claimed is:

1. A system for repairing lumen defects, the system comprising:

a deployment catheter; and a stent/graft including a proximal end portion and a distal end portion extending from the proximal end portion, the distal end portion having a cross-sectional thickness and a recess formed in and limited to the distal end portion of the stent/graft, the recess having a depth that is less than the cross-sectional thickness of the distal end portion thereby providing the distal end portion with a section having a decreased thickness and being adapted for releasably engaging the deployment catheter, wherein the recess has a geometry such that the recess mates with a portion of the deployment catheter.

2. The system of claim 1, the stent/graft further comprising an inner surface, the recess being formed on the inner surface.

3. The system of claim 1, the stent/graft further comprising an outer surface, the recess being formed on the outer surface.

4. The system of claim 1, wherein the recess is a groove.

5. The system of claim 1, wherein the recess is a hemispherical notch.

6. The system of claim 1, wherein the stent/graft has a generally tubular configuration.

* * * * *

UNITED STATES PATENT AND TRADEMARK OFFICE
CERTIFICATE OF CORRECTION

PATENT NO.     : 6,685,735 B1
DATED          : February 3, 2004
INVENTOR(S)    : Frederick Ahari It is certified that error appears in the above-identified patent and that said Letters Patent is hereby corrected as shown below:

<u>Title page, Item [54], Title, and Column 1, line 1,</u>
Title, delete "SYENT" and insert -- STENT --.

Signed and Sealed this

Seventeenth Day of August, 2004

JON W. DUDAS
*Acting Director of the United States Patent and Trademark Office*